United States Patent [19]

Kato et al.

[11] 4,245,128

[45] Jan. 13, 1981

[54] PROCESS FOR CLEAVING DIHYDROXYDIPHENYL ALKANES

[75] Inventors: Nobukatu Kato, Tokai; Tsutomu Takase, Nagoya; Yoshio Morimoto, Tokai; Teruo Yuasa; Minoru Hattori, both of Nagoya, all of Japan

[73] Assignee: Mitsui Toatsu Chemicals, Inc., Tokyo, Japan

[21] Appl. No.: 62,810

[22] Filed: Aug. 1, 1979

[30] Foreign Application Priority Data

Aug. 14, 1978 [JP] Japan .................................. 53-98268

[51] Int. Cl.$^3$ ............................................ C07C 37/52
[52] U.S. Cl. ................................................... 568/806
[58] Field of Search ........................ 568/743, 753, 806

[56] References Cited

U.S. PATENT DOCUMENTS 4,131,749  12/1978  Kiedik et al. ......................... 568/806

FOREIGN PATENT DOCUMENTS 880895  10/1961  United Kingdom ..................... 568/806
905994   8/1962  United Kingdom ..................... 568/806

OTHER PUBLICATIONS

Derent Belgian Patent Report, vol. 62 B, P. A15, (May 4, 1960).

Primary Examiner—Werren B. Lone
Attorney, Agent, or Firm—Sherman & Shalloway

[57] ABSTRACT

A novel process for producing alkenyl phenols, which comprises continuously feeding a dihydroxydiphenyl alkane such as 2,2-(4,4'-dihydroxydiphenyl)propane, 2,2-(4,4'-dihydroxy-3,3'-dimethyldiphenyl)propane, 2,2-(4,4'-dihydroxydiphenyl)butane, 2,2-(4,4'-dihydroxydiphenyl)-4-methylpentane, 1,1,1-(4,4'-dihydroxytriphenyl)ethane and 1,1-(4,4'-dihydroxydiphenyl)cyclohexane into a high-boiling inert organic reaction medium such as an alkylnaphthalene containing a basic catalyst and heated at 150° to 250° C. under 10 to 100 mmHg while maintaining the concentration of the dihydroxydiphenyl alkane in the reaction medium at not more than 30% by weight, thereby cleaving it in the reaction medium; and continuously distilling off the cleavage product out of the reaction system and recovering it. This process can afford the corresponding highly pure alkenyl phenol as a monomer and/or its polymer almost quantitatively.

14 Claims, No Drawings

PROCESS FOR CLEAVING DIHYDROXYDIPHENYL ALKANES

This invention relates to a process for producing an alkenyl phenol and/or its polymer by cleaving a dihydroxydiphenyl alkane.

It is well known that dihydroxydiphenyl alkanes are cleaved by heating them in the presence of basic catalyst to afford phenol and alkenyl phenols, and various methods have been suggested for producing alkenyl phenols by a cleaving reaction. However, all of the prior methods involved liquefying or vaporizing dihydroxydiphenyl alkanes without using a reaction medium and contacting the liquid or vapor with a basic catalyst.

For example, British Pat. No. 905,994 discloses a method which comprises adding sodium hydroxide to dihydroxydiphenyl propane, heating the mixture at 180° to 260° C. under reduced pressure to melt it, and rapidly cooling the cleavage product that distills off thereby to solidify it, and a method which comprises evaporating dihydroxydiphenyl propane by a liquid film-type evaporator at 260° C., passing the evaporated product through a catalyst bed of soda lime to decompose it in the gaseous phase, and rapidly cooling the product, and recovering the solidified product. However, no method has been known in the past which uses a reaction medium at the time of cleavage.

The cleavage reaction of dihydroxydiphenyl alkanes for the production of alkenyl phenols requires latent heat of evaporation for vaporizing the product and taking it out of the reaction system in addition to the energy required for cleavage. The amount of energy required for these is enormous. For this reason, when the dihydroxidiphenyl alkane is cleaved in the liquid state as in known methods, it is difficult to supply such a large amount of energy to the reaction system. Another defect in the known methods is that since the concentration of the starting material in the system is high, a part of the starting material distills off uncleaved together with the cleavage product. Furthermore, side-reactions, such as dealkylation of the resulting alkenyl phenol or conversion of the starting material and/or the product into a resin owing to localized overheating, take place. As a result, the yield of the desired product decreases, and inclusion of by-products in the final products reduces its purity. Thus, the cleavage reaction of dihydroxydiphenyl alkanes with basic catalysts poses various problems in commercial practice although it is a well-known reaction.

It is an object of this invention to provide a process for easily producing an alkenyl phenol commercially, as a result of solving the aforesaid problems associated with the production of alkenyl phenols by the cleavage of dihydroxydiphenyl alkanes in the presence of basic catalysts.

The above object of this invention is achieved by a process for producing an alkenyl phenol and/or its polymer by the cleavage of a dihydroxydiphenyl alkane in the presence of a basic catalyst, which comprises continuously feeding said dihydroxydiphenyl alkane into an inert organic reaction medium containing said basic catalyst and heated under reduced pressure, at such a rate that the concentration of said dihydroxydiphenyl alkane in the reaction medium is maintained at not more than 30% by weight, thereby cleaving the dihydroxydiphenyl alkane in the reaction medium; and distilling off the cleavage product continuously out of the reaction system and recovering it.

The dihydroxydiphenyl alkane used in the process of this invention is a gem (geminate)-dihydroxydiphenyl derivative of an aliphatic or alicyclic hydrocarbon containing 2 to 7 carbon atoms and being optionally substituted with a phenyl group, each hydroxyphenyl group being optionally substituted with one alkyl group containing 1 to 4 carbon atoms. Specific examples of the dihydroxydiphenyl alkane include 2,2-(4,4'-dihydroxydiphenyl)propane, 2-(4-hydroxyphenyl)-2-(2'-hydroxyphenyl)propane, 2,2-(4,4'-dihydroxy-3,3'-dimethyldiphenyl)propane, 2,2-(4,4'-dihydroxy-3-methyldiphenyl)propane, 1,1-(4,4'-dihydroxydiphenyl)ethane, 1,1-(4,4'-dihydroxydiphenyl)propane, 1,1-(4,4'-dihydroxydiphenyl)butane, 2,2-(4,4'-dihydroxydiphenyl)butane, 2,2-(4,4'-dihydroxydiphenyl)-3-methylbutane, 1,1-(4,4'-dihyroxydiphenyl)-2-methylpropane, 2,2-(4,4'-dihydroxydiphenyl)pentane, 3,3-(4,4'-dihydroxydiphenyl)pentane, 2,2-(4,4'-dihydroxydiphenyl)-4-methylpentane, 4,4-(4,4'-dihydroxydiphenyl)heptane, 1,1-(4,4'-dihydroxydiphenyl)cyclohexane, 1,1,1-(4,4'-dihydroxytriphenyl)ethane, and 2,2-(2,2'-dihydroxy-4,4'-di-t-butyldiphenyl)propane.

Not only dihydroxydiphenyl alkanes of high purity, but also those containing a tarry by-product which is the condensation reaction product between a phenol and a ketone formed in the production of the dihydroxydiphenyl alkanes from phenols and ketones can be used in the present invention as a starting material. To cleave the dihyroxydiphenyl alkane in the process of this invention, the inert organic reaction medium must be heated to a sufficient temperature for the smooth cleavage of the dihydroxydiphenyl alkane to phenol and an alkenyl phenol. Usually, this temperature is preferably in the range of 150° to 250° C. When the temperature of the inert organic reaction medium is lower than 150° C., the cleavage of the dihyroxydiphenyl alkane is markedly retarded, and the reaction time is prolonged. Furthermore, a part of the dihydroxydiphenyl alkane distills off uncleaved and gets mixed with the product to reduce the purity of the desired product. When the temperature of the inert organic reaction medium is higher than 250° C., side-reactions, such as dealkylation of the resulting alkenyl phenol or conversion of the starting material and/or the product into a resin, tend to take place to reduce the yield and purity of the product. Temperatures in the range of 200° to 240° C. are especially preferred because the formation of by-products is reduced and the cleavage reaction proceeds smoothly.

Furthermore, in the above cleavage reaction, the cleavage product must be rapidly distilled off out of the reaction system after it is formed. For this purpose, the cleavage reaction system or the inert organic reaction medium must be maintained under reduced pressure.

The degree of pressure reduction varies depending upon the cleavage temperature, but usually, the preferred cleavage pressure is in the range of 10 to 100 mmHg. If the pressure is lower than 10 mmHg, a part of the starting dihydroxydiphenyl alkane or a part of the inert organic reaction medium distills off together with the cleavage product, and gets mixed with the product, tending to reduce its purity. When the pressure is higher than 100 mmHg, it is difficult to distill off the cleavage product out of the reaction system, and consequently, the residence time of the product in the reaction system is prolonged. Thus, for example, side reactions such as dealkylation of the resulting alkenyl phenol tend to take place to reduce the yield of the desired product, and the by-products may get mixed with the desired product to decrease its purity. To distill off the cleavage product rapidly out of the reaction system and perform the reaction smoothly, pressures in the range of 50 to 100 mmHg are preferred, and those in the range of 50 to 80 mmHg are especially preferred.

To perform the cleavage reaction of the dihydroxydiphenyl alkane at the aforesaid temperature and pressure, the inert organic reaction medium is suitably a high-boiling inert organic solvent which has a melting or softening point of not more than 150° C., and a lower vapor pressure than the vapor pressure of the resulting alkenyl phenol at the temperature of cleaving the dihydroxydiphenyl alkane. More specifically, high-boiling inert organic solvents having a vapor pressure at 250° C. of not more than 100 mmHg are suitable. Examples of these organic solvents are hydrocarbon-type heat transfer media such as alkylnaphthalenes (KSK-Oil and Neo SK-Oil are available as commercial products made by Souken Kagaku Co. Inc.); high-boiling substances formed as by-products of a condensation reaction between phenols and ketones, for example the residues of a distillation tower or extraction tower which are left after separation of bisphenol A by distillation or extraction from the reaction product of phenol and acetone in the production of bisphenol A (to be referred to as bisphenol A distillation residue); and novolak-type phenolic resins having a softening point, determined by JIS K-2531 (JIS denotes Japanese Industrial Standards), of 60° to 150° C. obtained by condensing formaldehyde with an excess of phenol or cresol in the presence of an acid.

These reaction media well dissolve the dihydroxydiphenyl alkanes at the above-specified cleaving reaction temperatures.

The basic catalysts used in the process of this invention include, for example, oxides, hydroxides or carbonates of alkali metals or alkaline earth metals, such as sodium hydroxide, potassium hydroxide, sodium carbonate, potassium carbonate, calcium oxide and calcium hydroxide; alkali metal salts of phenols, such as sodium phenoxide, or a sodium salt of a condensation product formed between phenol or cresol and acetone (e.g., bisphenol A); and alkali metal salts of weakly acidic fatty acids such as sodium acetate. The suitable amount of the basic catalyst is 0.01 to 5% by weight based on the reaction medium.

The cleavage reaction of the dihydroxydiphenyl alkane in the process of this invention is effected by feeding the reaction medium and basic catalyst into a reactor equipped with a feed inlet for a starting material, a distillation outlet for a cleavage product, a thermometer, and optionally a stirring (or mixing) device, maintaining the reaction medium containing the basic catalyst at an elevated temperature, preferably 150° to 250° C., under a reduced pressure, preferably 10 to 100 mmHg, and feeding the dihydroxydiphenyl alkane. As a result, the dihyroxydiphenyl alkane dissolves in the reaction medium, and is cleaved in the presence of the basic catalyst dissolved in the reaction medium to form the corresponding alkenyl phenol and phenol. These products are vaporized, and rapidly distilled off out of the reaction system.

In the process of this invention, it is essential that in the above operation, the dihydroxydiphenyl alkane should be continuously fed into the reaction medium at such a rate that the concentration of the dihydroxydiphenyl alkane in the reaction medium is maintained at not more than 30% by weight. If the dihydroxydiphenyl alkane is fed at such a high rate that its concentration in the reaction medium exceeds 30% by weight, the distillation of the uncleaved starting material will increase. Furthermore, in such a case, supplying of heat in a sufficient amount for the distillation of the cleavage product fails, and the amount of the cleavage product that builds up in the reaction system increases to cause side-reactions such as conversion of the product to a resin or its dealkylation, resulting in reduced yields. Accordingly, the residence time of the cleavage product in the reaction system must be shortened by maintaining the concentration of the dihydroxydiphenyl alkane in the reaction medium at not more than 30% by weight.

The cleaving reaction of the dihydroxydiphenyl alkane and the distillation of the cleavage product proceed especially smoothly, and good results can be obtained, when the concentration of the dihydrocydiphenyl alkane in the reaction medium is in the range of 2 to 15% by weight.

The concentration of the dihydroxydiphenyl alkane in the reaction medium can easily be determined by, for example, gas chromatography.

Stirring (mixing) of the reaction medium with the starting material and the catalyst is possible by an ordinary mechanical method. In the process of this invention, however, it is advantageous to bubble an inert gas such as nitrogen, carbon dioxide, helium or argon through the reaction medium. Consequently, the reaction medium is stirred (mixed) to make the cleavage of the dihydroxydiphenyl alkane proceed smoothly and facilitate the distillation of the cleavage product out of the reaction system.

The cleavage product which distills off out of the reaction system is a mixture of phenol and alkenyl phenol. It can be easily recovered by cooling and condensation. At this time, a part of the alkenyl phenol may polymerize to a polymer of alkenyl phenol.

Thus, by performing the cleavage of the dihyroxydiphenyl alkane in the reaction medium while maintaining its concentration in the reaction medium at not more than 30% by weight, the efficiency of heat transfer increases, and it is easy to supply a large amount of energy required for the cleavage reaction and the distillation of the resulting alkenyl phenol. Moreover, this makes possible the avoidance of localized overheating. Accordingly, in the process of this invention, the temperature at which the dihydroxydiphenyl alkane is cleaved can be easily controlled. Consequently, the cleavage reaction of the dihydroxydiphenyl alkane proceeds smoothly, and the resulting alkenyl phenol can be distilled off out of the reaction system quickly without causing it to stay in the reaction system for an unduly long period of time.

Since the process of this invention enables the dihydroxydiphenyl alkane to be cleaved effectively, alkenyl phenols of high purity can be obtained almost quantitatively.

The following examples specifically illustrate the process of this invention. In these examples, all percentages are by weight.

EXAMPLE 1

A reactor (capacity 1 liter) equipped with a feed inlet for a starting material, a distillation outlet for a cleavage product, an inlet tube (bubbling tube) for an inert gas and a thermometer was charged with 80 g (the depth of liquid 3.0 cm) of KSK-Oil (a product of Souken Kagaku Co. Inc.) and 0.08 g of sodium hydroxide. The temperature of the KSK-Oil was maintained at 240° C., and the inside of the reactor was maintained at a pressure of 50 mmHg. Molten bisphenol A was continuously fed from the feed inlet at a rate of 400 g/hr into the KSK-Oil. In the meantime, nitrogen gas was introduced from the inlet tube at a rate of 4 liters/min., and bubbled through the KSK-Oil. Consequently, the cleavage reaction of bisphenol A and the distillation of the cleavage product out of the reactor proceeded smoothly, and the concentration of bisphenol A in the KSK-Oil was maintained at an average of 12.6%.

The cleavage product which was distilled out of the reactor was cooled to condense it, and recovered.

The above reaction was performed for 10 hours to cleave 4,000 g of bisphenol A. There was obtained 3,980 g of the cleavage product in a yield of 99.5%. The cleavage product was found to consist of 41.0% of phenol, 27.1% of p-isopropenyl phenol, 30.6% of p-isopropenyl phenol dimer and 1.3% of p-isopropenyl phenol trimer.

EXAMPLE 2

The same reactor was described in Example 1 was charged with 80 g (the depth of liquid 2.9 cm) of a bisphenol A distillation residue and 0.08 g of sodium hydroxide. Under the same conditions as in Example 1, 4000 g of bisphenol A was cleaved in the reactor. The concentration of bisphenol A in the reaction medium was maintained at 13%. There was obtained 3990 g of a cleavage product in a yield of 99.8%. The cleavage product was found to consist of 41.1% of phenol, 27.5% of p-isopropenyl phenol, 31.1% of p-isopropenyl phenol dimer, and 0.3% of p-isopropenyl phenol trimer.

EXAMPLES 3 TO 5

The same reactor as used in Example 1 was charged with 80 g (the depth of liquid 2.9 cm) of a bisphenol A distillation residue, and bisphenol A was cleaved under the conditions indicated in Table 1, in which the cleaving temperature refers to the temperature of the bisphenol A distillation residue, and the cleaving pressure, to the pressure of the inside of the reactor. During the reaction, nitrogen gas was introduced from the inlet tube at a rate of 4.0 liters/min. and bubbled through the bisphenol A distillation residue.

The results are shown in Table 2.

TABLE 2

| Example | Cleavage product Amount (g) | Cleavage product Yield (%) | Composition of the cleavage product Phenol (%) | Composition of the cleavage product Monomer* (%) | Composition of the cleavage product Dimer* (%) | Composition of the cleavage product Trimer* (%) |
|---|---|---|---|---|---|---|
| 3 | 2955 | 98.5 | 41.1 | 27.0 | 30.7 | 1.2 |
| 4 | 4975 | 99.5 | 41.1 | 27.2 | 31.0 | 0.7 |
| 5 | 4980 | 99.5 | 41.0 | 27.6 | 30.9 | 0.5 |

*:Monomer, dimer and trimer denote the monomer, a dimer and trimer of p-isopropenyl phenol.

EXAMPLE 6

The same reactor as described in Example 1 was charged with 80 g (the depth of liquid 2.9 cm) of a novolak resin having a softening point, measured by JIS K-2531, of 90° C., and 0.08 g of sodium hydroxide. Under the same conditions as in Example 1, 4000 g of bisphenol A was cleaved. The concentration of bisphenol A in the reaction medium was maintained at 12.5%. There was obtained 3950 g of a cleavage product in a yield of 98.8%. The cleavage product was found to consist of 41.0% of phenol, 27.0% of p-isopropenyl phenol, 30.9% of p-isopropenyl phenol dimer, and 1.1% of p-isopropenyl phenol trimer.

COMPARATIVE EXAMPLE 1

The same reactor as described in Example 1 was charged with 0.08 g of sodium hydroxide. The inside of the reactor was maintained at a temperature of 240° C. and a pressure of 50 mmHg. Molten bisphenol A was continuously fed into the reactor at a rate of 400 g/hr from the feed inlet.

When 800 g of bisphenol A was treated by the above procedure, the amount of the resulting cleavage product was only 500 g, and 300 g of a tarry substance deposited in the reactor. The yield of the product was 62.5%. The resulting cleavage product was found to consist of 55.5% of phenol, 5.1% of p-isopropenyl phenol, 4.2% of p-isopropenyl phenol dimer, and 35.2% of high-boiling substances.

COMPARATIVE EXAMPLE 2

2000 g of bisphenol A was treated under the same conditions as in Example 1 except that the feed rate of bisphenol A was set at 2000 g/hr, and the concentration of bisphenol A in the reaction medium was maintained at 50%.

There was obtained 1676 g (yield 83.8%) of a cleavage product. The cleavage product was found to consist of 33.6% of phenol, 20% of bisphenol, 23.9% of p-isopropenyl phenol, and 22.5% of p-isopropenyl phenol dimer.

TABLE 1

| Example | Basic catalyst Type | Basic catalyst Amount (g) | Cleaving temperature (°C.) | Cleaving pressure (mm/Hg) | Feed rate of bisphenol A (g/hr) | Concentration of bisphenol A (wt. %) | Cleaving time (hr) | Total amount of bisphenol A fed (g) |
|---|---|---|---|---|---|---|---|---|
| 3 | Potassium hydroxide | 0.11 | 210 | 30 | 300 | 28 | 10 | 3,000 |
| 4 | Sodium salt of bisphenol A | 0.31 | 245 | 70 | 500 | 15 | 10 | 5,000 |
| 5 | Sodium hydroxide | 0.08 | 250 | 100 | 500 | 5 | 10 | 5,000 |

EXAMPLE 7

The same reactor as described in Example 1 was charged with 80 g (the depth of liquid 2.9 cm) of a bisphenol A distillation residue and 0.08 g of sodium hydroxide, and under the same conditions as in Example 1, 4000 g of 2,2-(4,4'-dihydroxy-3,3'-dimethyldiphenyl)propane was cleaved. The concentration of the starting material in the reaction medium was maintained at 15%. There was obtained 3990 g of a cleavage product in a yield of 99.75%. The cleavage product was found to consist of 42.0% of o-cresol, 52.2% of p-isopropenyl-o-cresol, 4,06% of p-isopropenyl-o-cresol dimer, and 1.74% of p-isopropenyl-o-cresol trimer.

EXAMPLE 8

The same reactor as described in Example 1 was charged with 80 g (the depth of liquid 3.0 cm) of KSK-Oil (a product of Souken Kagaku Co. Inc.) and 0.08 g of sodium hydroxide. Under the same conditions as in Example 1, 4000 g of 2,2-(4,4'-dihydroxy-3-methyldiphenyl)propane was cleaved. The concentration of the starting material in the reaction medium was maintained at 13%. There was obtained 3995 g of a cleavage product in a yield of 99.8%. The cleavage product was found to consist of 18.2% of phenol, 28.0% of o-cresol, 31.3% of p-isopropenyl phenol, and 22.5% of p-isopropenyl-o-cresol.

EXAMPLE 9

The same reactor as described in Example 1 was charged with 80 g (the depth of liquid 2.9 cm) of a bisphenol A distillation residue and 0.08 g of sodium hydroxide. Under the same conditions as in Example 1, 4000 g of 2,2-(4,4'-dihydroxydiphenyl)butane was cleaved. The concentration of the starting material in the reaction medium was maintained at 15%. There was obtained 3960 g of a cleavage product in a yield of 99.0%. The cleavage product was found to consist of 38.9% of phenol and 61.1% of 2-(4-hydroxyphenyl)-butene-2.

EXAMPLE 10

The same reactor was described in Example 1 was charged with 80 g (the depth of liquid 2.9 cm) of a bisphenol A distillation residue and 0.08 g of sodium hydroxide. Under the same conditions as in Example 1, 4000 g of 2,2-(4,4'-dihydroxydiphenyl)-4-methylpentane was cleaved. The concentration of the starting material in the reaction medium was maintained at 20%.

There was obtained 3970 g of a cleavage product in a yield of 99.3%. The cleavage product was found to consist of 26% of phenol and 74% of 2-(4-hydroxyphenyl)-4-methylpentene-2.

EXAMPLE 11

The same reactor as described in Example 1 was charged with 80 g (the depth of liquid 2.9 cm) of a bisphenol A distillation residue and 0.08 g of sodium hydroxide, and under the same conditions as in Example 1, 4000 g of 1,1,1-(4,4'-dihydroxydiphenyl)ethane was cleaved. The concentration of the starting material in the reaction medium was maintained at 20%.

There was obtained 3990 g of a cleavage product in a yield of 99.8%. The cleavage product was found to consist of 32.4% of phenol and 67.6% of alpha-(p-hydroxyphenyl)styrene.

EXAMPLE 12

Under the same conditions as in Example 11, 1,1-(4,4'-dihydroxydiphenyl)cyclohexane was cleaved. The yield of the product was 99.9%. The cleavage product was found to consist of 35.9% of phenol and 64.1% of 1-(4-hydroxyphenyl)-cyclohexane-1.

What we claim is:

1. A process for cleaving dihydroxydiphenyl alkane to produce an alkenyl phenol, alkenyl phenol polymer and mixtures thereof, which comprises continuously feeding said dihydroxydiphenyl alkane into an inert organic solvent reaction medium containing a basic catalyst wherein said basic catalyst is an oxide, hydroxide or carbonate of an alkali metal or an alkaline earth metal, an alkali metal salt of phenol or bisphenol A, or an alkali metal salt of a weakly acidic fatty acid, heating the reaction mixture at a temperature of 150° to 250° C. and at a pressure of 10 to 100 mmHg, maintaining the concentration of said dihydroxydiphenyl alkane in the reaction medium at not more than 30% by weight, cleaving said dihydroxydiphenyl alkane in said reaction medium; and continuously distilling the cleavage product out of the reaction system and recovering it.

2. The process of claim 1 wherein said inert organic reaction medium is heated at 150° to 250° C. under 50 to 100 mmHg.

3. The process of claim 1 wherein said inert organic reaction medium is heated at 200° to 240° C. under 50 to 80 mmHg.

4. The process of claim 2 wherein said inert organic reaction medium is a high-boiling inert organic solvent which has a melting or softening point of not more than 150° C. and a lower vapor pressure at the cleaving temperature of the dihydroxydiphenyl alkane than the vapor pressure of the alkenyl phenol.

5. The process of claim 2 wherein said inert organic reaction medium is a hydrocarbon-type heat transfer medium, a distillation tower residue or extraction tower residue left after the separation of bisphenol A by distillation or extraction from the reaction product of phenol and acetone in the production of bisphenol A, or a novolak-type phenolic resin having a softening point of 60° to 150° C. obtained by condensing formaldehyde with an excess of phenol or cresol in the presence of an acid.

6. The process of claim 2 wherein said basic catalyst is an oxide, hydroxide or carbonate of an alkali metal or an alkaline earth metal, an alkali metal salt of phenol or bisphenol A, or an alkali metal salt of a weakly acidic fatty acid, and is used in an amount of 0.01 to 5% by weight based on the weight of the inert organic reaction medium.

7. The process of claim 5 wherein said basic catalyst is sodium hydroxide, potassium hydroxide or a sodium salt of bisphenol A, and is used in an amount of 0.05 to 0.5% by weight based on the weight of the inert organic reaction medium.

8. The process of claim 7 wherein said dihydroxydiphenyl alkane is continuously fed at such a rate that its concentration in the inert organic reaction medium is maintained at 2 to 15% by weight.

9. The process of claim 2 wherein said dihydroxydiphenyl alkane is a gem-dihydroxydiphenyl derivative of an aliphatic or alicyclic hydrocarbon containing 2 to 7 carbon atoms and optionally containing a phenyl group as a substituent, each hydroxyphenyl group thereof being optionally substituted with one alkyl group containing 1 to 4 carbon atoms.

10. The process of claim 2 wherein said dihydroxydiphenyl alkane is 2,2-(4,4'-dihydroxydiphenyl)propane, 2-(4-hydroxyphenyl)-2-(2'-hydroxyphenyl)propane, 2,2-(4,4'-dihydroxy-3,3'-dimethyldiphenyl)propane, 2,2-(4,4'-dihydroxy-3-methyldiphenyl)propane, 1,1-(4,4'-dihydroxydiphenyl)ethane, 1,1-(4,4'-dihydroxydiphenyl)propane, 1,1-(4,4'-dihydroxydiphenyl)butane, 2,2-(4,4'-dihydroxydiphenyl)butane, 2,2-(4,4'-dihydroxydiphenyl)-3-methylbutane, 1,1-(4,4'-dihydroxydiphenyl)-2-methylpropane, 2,2-(4,4'-dihydroxydiphenyl)pentane, 3,3-(4,4'-dihydroxydiphenyl)pentane, 2,2-(4,4'-dihydroxydiphenyl)-4-methylpentane, 4,4-(4,4'-dihydroxydiphenyl)heptane, 1,1-(4,4'-dihydroxydiphenyl)cyclohexane, 1,1,1-(4,4'-dihydroxytriphenyl)ethane or 2,2-(2,2'-dihydroxy-4,4'-di-t-butyldiphenyl)propane.

11. A process for cleaving dihydroxydiphenyl alkane to produce an alkenyl phenol, alkenyl phenol polymer and mixtures thereof, which comprises continuously feeding said dihydroxydiphenyl alkane into an inert reaction medium consisting of high-boiling inert organic solvent which has a melting or softening point of not more than 150° C. and a lower vapor pressure at the cleaving temperature of the dihydroxydiphenyl alkane than the vapor pressure of the alkenyl phenol, said reaction medium containing a basic catalyst selected from the group consisting of alkali metal oxide, hydroxide and carbonate, alkaline earth metal, alkali metal salt of phenol and bisphenol A, and alkali metal salt of a weakly acidic fatty acid, in an amount of 0.01 to 5% by weight based on the weight of the inert organic reaction medium, heating the reaction mixture at a temperature of 150° to 250° C. and at a pressure of 10 to 100 mmHg, maintaining the concentration of said dihydroxydiphenyl alkane in the reaction medium at not less than 2% and not more than 30% by weight, cleaving said dihydroxydiphenyl alkane in said reaction medium; and continuously distilling the cleavage product out of the reaction system and recovering it.

12. The process of claim 11 wherein said inert organic reaction medium is a hydrocarbon-type heat transfer medium, a distillation tower residue or extraction tower residue left after the separation of bisphenol A by distillation or extraction from the reaction product of phenol and acetone in the production of bisphenol A, or a novolac-type phenolic resin having a softening point of 60° to 150° C. obtained by condensing formaldehyde with an excess of phenol or cresol in the presence of an acid.

13. The process of claim 11 wherein said dihydroxydiphenyl alkane is continuously fed at such a rate that its concentration in the inert organic reaction medium is maintained at 2 to 15% by weight.

14. The process of claim 11 wherein said dihydroxydiphenyl alkane is a gem-dihydroxydiphenyl derivative of an aliphatic or alicyclic hydrocarbon containing 2 to 7 carbon atoms and optionally containing a phenyl group as a substituent, each hydroxyphenyl group thereof being optionally substituted with one alkyl group containing 1 to 4 carbon atoms.

* * * * *